US012485063B1

(12) United States Patent
Chen

(10) Patent No.: US 12,485,063 B1
(45) Date of Patent: Dec. 2, 2025

(54) SENSOR CONTROL METHOD AND CONTACT-BASED DEVICE

(71) Applicant: UC GLOBAL TRADE INC., Chino, CA (US)

(72) Inventor: Junjun Chen, Shenzhen (CN)

(73) Assignee: UC GLOBAL TRADE INC., Chino, CA (US)

( * ) Notice: Subject to any disclaimer, the term of this patent is extended or adjusted under 35 U.S.C. 154(b) by 0 days.

(21) Appl. No.: 19/245,783

(22) Filed: Jun. 23, 2025

(30) Foreign Application Priority Data

May 22, 2025 (CN) ......................... 202510664896.1

(51) Int. Cl.
*A61H 23/02* (2006.01)
*G16H 40/40* (2018.01)

(52) U.S. Cl.
CPC ............. *A61H 23/02* (2013.01); *G16H 40/40* (2018.01); *A61H 2201/5071* (2013.01)

(58) Field of Classification Search
CPC . A61H 23/02; A61H 2201/5071; G16H 40/40
See application file for complete search history.

(56) References Cited

FOREIGN PATENT DOCUMENTS

| | | |
|---|---|---|
| CN | 102935031 B | 5/2014 |
| CN | 205108304 U | 3/2016 |
| CN | 213911253 U | 8/2021 |
| CN | 117205064 A | 12/2023 |
| CN | 119868132 B | 5/2025 |

*Primary Examiner* — Mohammad Ali
*Assistant Examiner* — Sheela Rao
(74) *Attorney, Agent, or Firm* — Ming Jiang; OPENPTO US LLC

(57) ABSTRACT

Disclosed is a sensor control method, including: initiating an adaptive range determination procedure in response to a first trigger instruction from a user; and obtaining detection data of the sensor when the user is using a contact-based device; where the sensor is integrated into the contact-based device; obtaining a maximum value of the detection data within a preset time period; and determining the maximum value of the detection data as a current maximum range value of the sensor; where the current maximum range value of the sensor shall not exceed an actual maximum range value of the sensor; and controlling the contact-based device based on the current maximum range value of the sensor.

19 Claims, 4 Drawing Sheets

SENSOR CONTROL METHOD AND CONTACT-BASED DEVICE

CROSS REFERENCE TO RELATED APPLICATIONS

The present application claims priorities of the Chinese Patent Application No. 2025106648961, filed on May 22, 2025, the content of which is hereby incorporated by reference in entirety.

TECHNICAL FIELD

The present disclosure belongs to the technical field of detection control, and relates to a sensor control method and a contact-based device.

BACKGROUND

A massager is a tool that provides massage or stimulation to human muscles, meridians and other body parts through mechanical vibration, current stimulation or other methods.

Structurally, different sensors are usually arranged in the massager to detect various data of the massager when it is used by a user, thereby achieving more precise massage control.

However, studies have identified that most of the sensors currently used in the massagers have fixed response patterns. Since different users have different expectations regarding the response of the massager, fixed sensor response procedures make it difficult to cater to individual needs, thereby affecting the user experience.

Moreover, the sensors suffer from some problems of ex-factory consistency. Due to factors such as assembly process and individual manufacturing errors, baseline data detected by the sensors may vary among the assembled products. As a result, different products of a same model may produce different use experience.

SUMMARY

In order to solve the above technical problems, the present disclosure provides a sensor control method and a contact-based device.

In order to achieve the above objectives, the present disclosure adopts the following technical solutions:

in a first aspect, the present disclosure provides a sensor control method, including: initiating an adaptive range determination procedure in response to a first trigger instruction from a user; and obtaining detection data of the sensor when the user is using a contact-based device; where the sensor is integrated into the contact-based device; obtaining a maximum value of the detection data within a preset time period; and determining the maximum value of the detection data as a current maximum range value of the sensor; where the current maximum range value of the sensor shall not exceed an actual maximum range value of the sensor; and controlling the contact-based device based on the current maximum range value of the sensor.

Optionally, the preset time period may include N usage cycles, where N is a positive integer; the obtaining a maximum value of the detection data within a preset time period includes: acquiring a maximum value of data from each of the N usage cycles, then calculating an average of N maximum values to obtain a maximum value of the detection data.

Optionally, a weighted average strategy is used to calculate the average of N maximum values to obtain a maximum value of the detection data.

Optionally, a closer a usage cycle is to a current time, a higher a weight is assigned.

Optionally, the determining the maximum value of the detection data as a current maximum range value of the sensor includes: increasing the maximum value of the detection data by a preset ratio, and determining the value after increase as the current maximum range value of the sensor.

Optionally, the value after increase is less than the actual maximum range value of the sensor, or when the value after increase is greater than the actual maximum range value of the sensor, the actual maximum range value of the sensor is determined as the value after increase.

Optionally, a range of the preset ratio is 1%-20%.

Optionally, the determining the maximum value of the detection data as a current maximum range value of the sensor may specifically include: decreasing the maximum value of the detection data by the preset ratio, and determining the value after decrease as the current maximum range value of the sensor.

Optionally, a range of the preset ratio is 1%-20%.

Optionally, the method further includes: acquiring a maximum value of the detection data from each operation cycle in M operation cycles, where M is a positive integer; and dynamically updating the current maximum range value of the sensor based on the maximum value of the detection data from each operation cycle in M operation cycles.

Optionally, each operation cycle takes power-on and power-off of the contact-based device as cycle nodes.

Optionally, the dynamically updating the current maximum range value of the sensor based on the maximum value of the detection data from each operation cycle in M operation cycles includes: increasing the current maximum range value of the sensor by a first preset value in response to a steadily increasing trend in the maximum value of the detection data of the sensor across each operation cycle in M operation cycles.

Optionally, the dynamically updating the current maximum range value of the sensor based on the maximum value of the detection data from each operation cycle in M operation cycles includes: decreasing the current maximum range value of the sensor by a second preset value in response to a steadily decreasing trend in the maximum value of the detection data of the sensor across each operation cycle in M operation cycles.

Optionally, the method further includes: initiating a range self-calibration procedure in response to a second trigger instruction from the user or a correction instruction from an operator; and acquiring a first detection value of the sensor when a fixture applies force to the contact-based device, where under standard conditions, the force applied by the fixture corresponds to a preset fixed value; and mapping the first detection value to the preset fixed value, and taking the preset fixed value as the actual maximum range value of the sensor.

Optionally, the method further includes: initiating a zero-point calibration procedure in response to a third trigger instruction from the user; acquiring a second detection value of the sensor when the contact-based device is in a stable state; and storing the second detection value in a memory, and taking the second detection value as a zero-point value.

Optionally, the method further includes: initiating a zero-point calibration procedure upon power-on of the contact-based device; acquiring a second detection value of the sensor when the contact-based device is in a stable state; and storing the second detection value in a memory, and taking the second detection value as a zero-point value.

Optionally, the method further includes: initiating a zero-point calibration procedure after the contact-based device has been used for a preset time period; acquiring a second detection value of the sensor when the contact-based device is in a stable state; and storing the second detection value in a memory, and taking the second detection value as a zero-point value.

Optionally, the method further includes: executing an initialization procedure to update the current maximum range value of the sensor in response to a fourth trigger instruction from the user.

In a second aspect, the present disclosure provides a contact-based device, including a main body, a controller disposed inside the main body, and a sensor disposed on the main body; where the controller is connected to the sensor; and the controller is configured to perform the following steps, comprising: initiating an adaptive range determination procedure in response to a first trigger instruction from a user; obtaining detection data of the sensor when the user is using a contact-based device; wherein the sensor is integrated into the contact-based device; obtaining a maximum value of the detection data within a preset time period; determining the maximum value of the detection data as a current maximum range value of the sensor; wherein the current maximum range value of the sensor is not greater than an actual maximum range value of the sensor; and controlling the contact-based device based on the current maximum range value of the sensor.

Optionally, the sensor is a pressure sensor.

The present disclosure has the following beneficial effects:

The present disclosure provides an adaptive range determination process for a sensor. The process uses the actual user experience data as a basis. When the user triggers the first trigger instruction, the detection data of the sensor during the operation of the contact-based device is collected, and a maximum value within the preset time period is determined as a current maximum range value of the sensor, and the contact-based device is controlled based on the current maximum range value of the sensor.

The process has the following beneficial effects: First, it can adapt to the user needs, such that a response range of the sensor first the actual usage status of the user (non-fixed). The above process can be used to control different products of the same type, so as to meet the user's needs in a consistent manner, such that the contact-based device can adapt to different individual users and achieve consistency of products based on the individual users.

Second, the above adaptive range determination is equivalent to reducing the actual range maximum value, such that the sensor can operate within a narrower working range, and a measurement resolution can be enhanced.

DETAILED DESCRIPTIONS OF THE EMBODIMENTS

The technical solutions of embodiments of the present disclosure will be described below clearly and comprehensively in conjunction with accompanying drawings of the embodiments of the present disclosure. Apparently, the embodiments described are merely some embodiments rather than all embodiments of the present disclosure. All the other embodiments obtained by those of ordinary skill in the art based on the embodiments in the present disclosure without creative efforts shall fall within the scope of protection of the present disclosure.

Studies have identified that most of the sensors currently used in the massagers have fixed response procedures. However, different users have different expectations regarding the response of the massagers, fixed sensor response procedures make it difficult to adapt to individual consumer needs, thereby affecting the user experience. Moreover, the sensors face some problems of ex-factory consistency. Due to factors such as assembly process and individual manufacturing errors, baseline data detected by the sensors may vary between the products that are assembled. As a result, different products of a same model may bring different use experience to the user.

Figure 1:
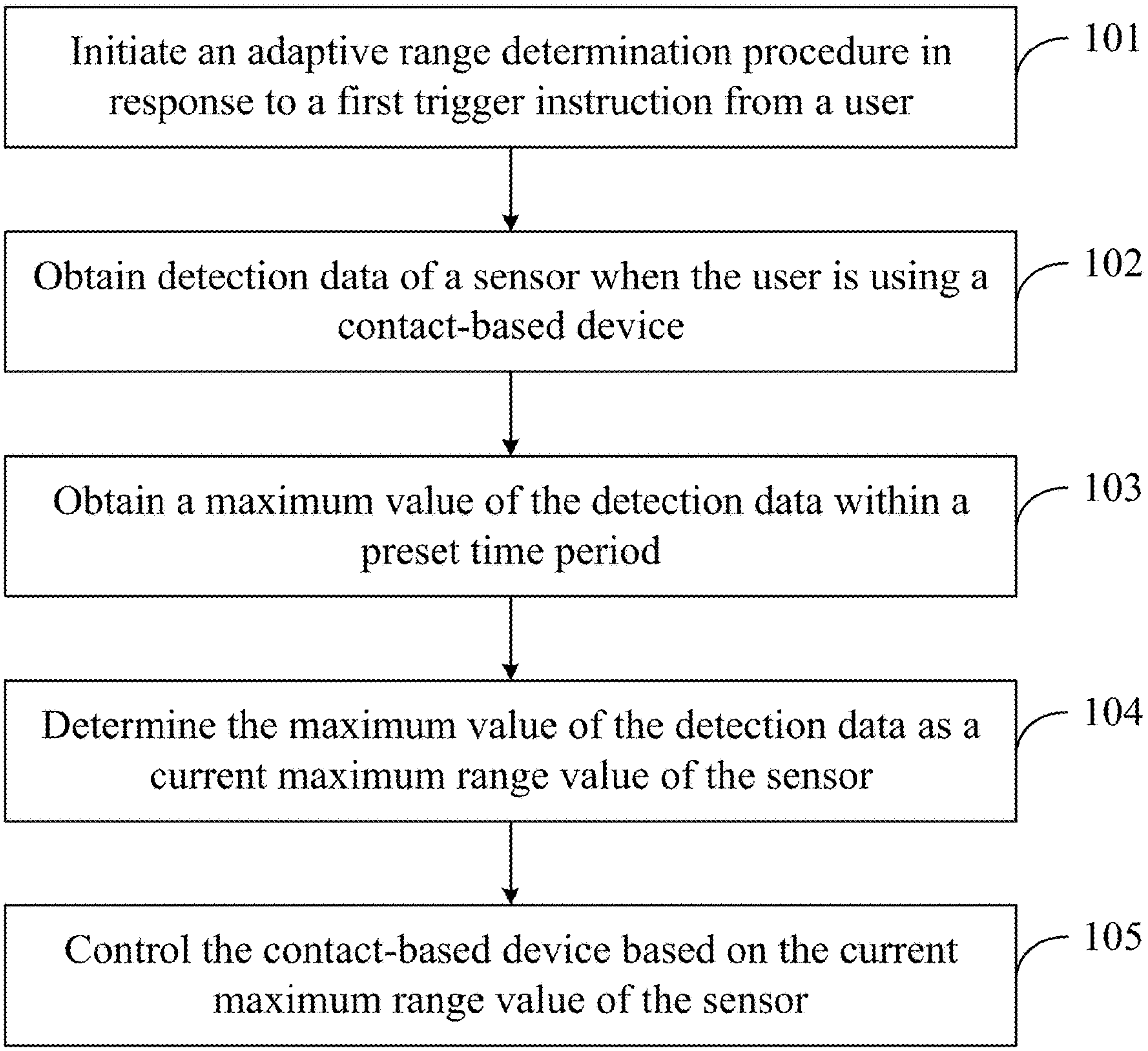
FIG. 1 is a flowchart of steps for a first sensor control method according to an embodiment of the present disclosure.

The present disclosure provides the following embodiments to solve the above problems:

With reference to FIG. 1, this embodiment provides a sensor control method, including steps 101-105.

Step 101: initiating an adaptive range determination procedure in response to a first trigger instruction from a user.

It should be noted that when using a contact-based device, the user may actively trigger the contact-based device to initiate the adaptive range determination procedure. The adaptive range determination procedure is mainly used to determine an adaptive range for the sensor.

Specifically, a button may be provided on the contact-based device; and the first trigger instruction may be represented after the user press the button for a plurality of consecutive times. The times for pressing the button may be set according to actual demands, such as 2, 3, and 5.

In this embodiment, the contact-based device may be a massage device. Specific structure and description of the contact-based device will be described in detail in the subsequent embodiments.

It should be further noted that the adaptive range determination procedure includes the following steps 102-104.

Step 102: obtaining detection data of the sensor when the user uses the contact-based device.

Specifically, the sensor is integrated into the contact-based device. Accordingly, the data of the sensor may be continuously collected when the user uses the contact-based device.

In this embodiment, the sensor integrated into the contact-based device may be a pressure sensor.

Of course, the sensor integrated into the contact-based device may also include, but is not limited to, a vibration sensor, an inertial measurement unit, and the like, which is not limited herein.

Step 103: obtaining a maximum value of the detection data within a preset time period.

The preset time period is detected. Specifically, the preset time period may be a first usage cycle of the user. For example, when the user receives the contact-based device and triggers the first trigger instruction, the time period before the device is powered off may serve as the preset time period for step 103.

Generally, when using the device for the first time, the user will try various functions. During this process, data of the sensor is continuously acquired, and a maximum value from the detection data is screened out.

Of course, the preset time period may be customized to a plurality of days or hours, for example, the preset time period may be 3 days, 5 days, 10 hours, 20 hours, and the like. Assuming that the preset time period is 3 days, the time that the first trigger instruction is triggered is defined as a starting node to obtain the detection data of the sensor within 3 days, and a maximum value from the detection data is screened out.

It should be noted that the maximum value of the detection data usually represents the maximum level the user can accept during use. For example, during the use for the first time, when the user increases the massage force of the contact-based device and stops one node, and a current force of the pressure sensor is 80 N, it can be inferred that a maximum tolerable force that the user can be accepted is 80 N (any further increase may cause discomfort to the user).

Step 104: determining the maximum value of the detection data as a current maximum range value of the sensor.

Specifically, the current maximum range value of the sensor shall not exceed an actual maximum range value of the sensor.

For example, when the sensor is a pressure sensor, an actual maximum range value of the sensor is 100 N, when the maximum value of the detection data is 80 N, then 80 N is determined as a current maximum range value of the sensor.

Step 105: controlling the contact-based device based on the current maximum range value of the sensor.

In the subsequent control processes of the contact-based device, the current maximum range value of the sensor is used as a boundary for control.

Taking the above example as an example, the current maximum range value 80 N of the sensor is used as the boundary for control.

Considering that the current contact-based device suffers from fixed sensor response procedure and lack of consistency (for example, products of the same type may have sensing ranges of 0-90 N or 0-100 N), this embodiment provides an adaptive range determination process for a sensor. The process uses the actual user experience data as a basis. When the user triggers the first trigger instruction, the detection data of the sensor during the operation of the contact-based device is collected, and a maximum value within the preset time period is determined as a current maximum range value of the sensor, and the contact-based device is controlled based on the current maximum range value of the sensor. The process has the following beneficial effects: First, it can adapt to the user needs, such that a response range of the sensor first the actual usage status of the user (non-fixed). The above process can be used to control different products of the same type, so as to meet the user's needs in a consistent manner, such that the contact-based device can adapt to different individual users and achieve consistency of products based on the individual users.

Second, the above adaptive range determination is equivalent to reducing the actual range maximum value, such that the sensor can operate within a narrower working range, and a measurement resolution can be enhanced. For example, as for the above embodiment, when the working range of the sensor is 0-80 N, the detection precision can be improved compared with the actual range of 0-100 N, making it easier to capture subtle changes.

Optionally, the preset time period may include N usage cycles, where N is a positive integer.

For example, N may be specifically 3, 5, or 7. One massage session that the user uses the contact-based device can be defined as one usage cycle. For example, when the user uses the contact-based device for 5 minutes, a period of the 5 minutes can be taken as one usage cycle. When the user pauses for a while and then uses the contact-based device for another 7 minutes, the another 7 minutes will be taken as another usage cycle.

Accordingly, the Step 103 of obtaining a maximum value of the detection data within a preset time period may specifically include: acquiring the maximum value of data from each of the N usage cycles, then calculating an average of N maximum values to obtain a maximum value of the detection data.

That is, in this embodiment, the average of the maximum values of the N usage cycles is used as a final maximum value of the detection data, and the average is then determined as the maximum value of the detection data for the preset time period.

It should be noted that using only a single usage cycle may lead to accidental data, which may affect the accuracy and rationality of subsequent control. Therefore, this embodiment adopts the average of the maximum values of the N usage cycles as the results. Furthermore, the average of the maximum values of the N usage cycles is closer to the user's actual needs, thereby further improving the accuracy of subsequent control.

On this basis, the maximum value of the detection data is obtained based on the average of the maximum values of the N usage cycles, a weighted average strategy may also be adopted. Specifically, different weights are assigned to each usage cycle based on its proximity to the current time point. Specifically, a closer a usage cycle is to a current time, a higher a weight is assigned. Therefore, a farther a usage cycle is from the current time point, a lower a weight is assigned to it.

For example, assuming that four usage cycles are collected, that is, a usage cycle A, a usage cycle B, a usage cycle C, and a usage cycle D. The usage cycles from the farthest to the nearest relative to the current time point are the usage cycle D, the usage cycle C, the usage cycle B, and the usage cycle A. The weights assigned in sequence are 0.2 for the usage cycle D, 0.23 for the usage cycle C, 0.27 for the usage cycle B, and 0.3 for the usage cycle A.

It should be noted that the above weighted average strategy can enhance the accuracy of the user's personalized adaptation, and the user will become more and more adapted to and use the contact-based device in a most comfortable force range during the process. Therefore, a closer a usage cycle is to a current time, a higher a weight is assigned, so as to better reflect the user's current needs and usage status.

Optionally, the Step 104 of determining the maximum value of the detection data as a current maximum range value of the sensor may specifically include: increasing the maximum value of the detection data by a preset ratio, and determining the value after increase as the current maximum range value of the sensor.

Specifically, the value after increase shall be less than the actual maximum range value of the sensor, or when the value after increase is greater than the actual maximum range value of the sensor, the actual maximum range value of the sensor is determined as the value after increase.

Specifically, the preset ratio can be set as needed, and a range of the preset ratio may be 1%-20%, for example, the preset ratio may be 10% or 20%, and the like. The purpose of setting the preset ratio is to dynamically reserve a buffer margin, and improve the control accuracy near the peak value of the contact-based device.

In one embodiment, when the value after increase is greater than the actual maximum range value of the sensor, the preset ratio may be adaptively reduced. For example, an initial default preset ratio is 10%. When a value after increase by 10% is greater than the actual maximum range value of the sensor, the preset ratio is adaptively reduced to 5%. When the value after increase by 5% is still greater than the actual maximum range value of the sensor, the preset ratio may be further adaptively reduced to 2%, and so on.

Optionally, the Step 104 of determining the maximum value of the detection data as a current maximum range value of the sensor may specifically include: decreasing the maximum value of the detection data by a preset ratio, and determining the value after decrease as the current maximum range value of the sensor.

Specifically, the preset ratio can be set as needed, and a range of the preset ratio may be 1%-20%, for example, the preset ratio may be 10% or 20%, and the like.

It should be noted that the maximum value of the detection data does not necessarily represent the actual pressure required by the user, but only the maximum pressure that the user can tolerate. A pressure range that the user commonly operates must be lower than the maximum pressure value. Therefore, in this embodiment, decreasing the maximum value of the detection data by the preset ratio, and determining the value after decrease as the current maximum range value of the sensor is expected to make the detection more accurate.

It should further be noted that the above different strategies may be selected based on the user's profile, or may be set according to different user categories, such as user group, which is not limited herein.

Figure 2:
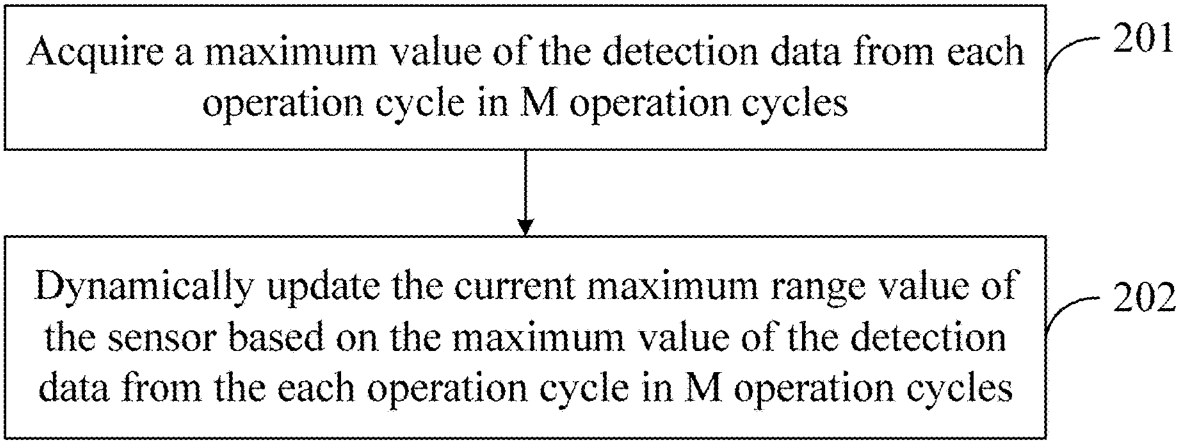
FIG. 2 is a flowchart of steps for a second sensor control method according to an embodiment of the present disclosure.

Optionally, with reference to FIG. 2, in one embodiment, the method further includes Steps 201-202.

Step 201: acquiring a maximum value of the detection data from each operation cycle in M operation cycles.

Specifically, each operation cycle takes power-on and power-off of the contact-based device as cycle nodes; where M is a positive integer.

M may be specifically 5, 10, or 20.

It should be noted that the M operation cycles differ from the preset time period in the previous embodiment, the preset time period characterizes short-term usage, while the M operation cycles represent long-term usage.

Step 202: dynamically updating the current maximum range value of the sensor based on the maximum value of the detection data from each operation cycle in M operation cycles.

This embodiment reflects that the current maximum range value of the sensor is dynamically fine-tuned based on the data obtained during the long-term use process, so as to ensure adaptation to the user's long-term use.

In other words, this embodiment provides a dynamic range update mechanism based on a complete operation cycle, which can track the long-term data of the contact-based device to continuously optimize and adapt to the user's usage state.

Optionally, the Step 202 of dynamically updating the current maximum range value of the sensor based on the maximum value of the detection data from each operation cycle in M operation cycles may specifically include the following two cases:

first case: in response to a steadily increasing trend in the maximum value of the detection data of the sensor across each operation cycle in M operation cycles, the current maximum range value of the sensor is increased by a first preset value.

The steadily increasing trend may refer to the condition where the maximum value of the detection data in each of the operation cycles increases sequentially, indicating that the user is applying an increasing pressure to the contact-based device, in which case, the current maximum range value of the sensor is increased by the first preset value. The first preset value may be set as required, for example, 5 N, 10 N, and the like.

Therefore, in this embodiment, the current maximum range value of the sensor is actively expanded according to the user's increasing pressure demand to follow the user's usage process, and the response range of the sensor is adjusted dynamically, thereby enabling dynamic tracking and adaptation.

Second case: in response to a steadily decreasing trend in the maximum value of the detection data of the sensor across each operation cycle in M operation cycles, the current maximum range value of the sensor is decreased by a second preset value.

The steadily decreasing trend may refer to the condition where the maximum value of the detection data in each of the operation cycles decreases sequentially, indicating that the user is applying a decreasing pressure to the contact-based device, in which case, the current maximum range value of the sensor is decreased by the second preset value. The second preset value may be set as required, for example, 5 N, 10 N, and the like. The second preset value may be the same as the first preset value, or may be different from the first preset value, which is not limited herein.

Therefore, in this embodiment, the current maximum range value of the sensor is actively reduced according to the user's decreasing pressure demand to follow the user's usage process, and the response range of the sensor is adjusted dynamically, thereby enabling dynamic tracking and adaptation and improving the detection accuracy.

Figure 3:
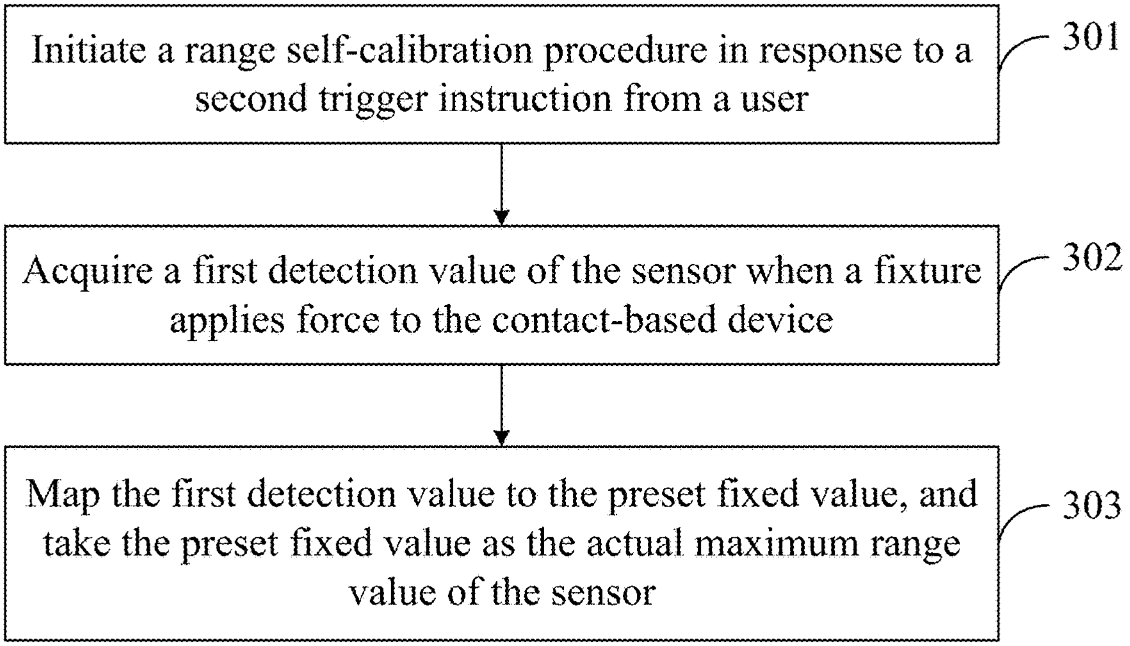
FIG. 3 is a flowchart of steps for a third sensor control method according to an embodiment of the present disclosure.

Optionally, with reference to FIG. 3, the method further includes Steps 301-303.

Step 301: initiating a range self-calibration procedure in response to a second trigger instruction from a user.

It should be noted that when using a contact-based device, the user may actively trigger the contact-based device to initiate the range self-calibration procedure. The range self-calibration procedure is primarily used to initialize or calibrate a range of the sensor.

Specifically, a button may be provided on the contact-based device; and the second trigger instruction may be represented after the user press the button for a plurality of consecutive times. The times for pressing the button may be set according to actual demands, such as 2, 3, and 5.

It should be noted that the second trigger instruction is different from the first trigger instruction. For example, pressing the button twice in succession may correspond to the first trigger instruction, while pressing the button three times in succession may correspond to the second trigger instruction.

Step 302: acquiring a first detection value of the sensor when a fixture applies force to the contact-based device.

Under standard conditions, the force applied by the fixture corresponds to a preset fixed value. For example, under standard conditions, when the force applied by the fixture is 100 N, the 100 N is the preset fixed value.

The fixture may be a device with a resilient structure, and the user needs to clamp the fixture at a position of the sensor of the contact-based device. Once the fixture is clamped and stabilized, the first detection value is acquired from the sensor.

Step 303: mapping the first detection value to the preset fixed value, and taking the preset fixed value as the actual maximum range value of the sensor.

For example, assuming that the preset fixed value is 100 N and the first detection value is 90 N, the first detection value of 90 N is mapped to the preset fixed value of 100 N to ensure product consistency. A new reading is calculated based on the above mapping relationship.

That is, considering the possible problems, such as drift, or product aging, arising from the usage of the sensor, or inconsistencies, or inconsistencies arising from the initialization or manufacturing of the sensor, this embodiment establishes a new mapping relationship by applying the preset fixed value using a fixture and comparing it to the actual detected reading of the sensor, such that nonlinear errors of the sensor are corrected, and potential control deviations are prevented.

Figure 4:
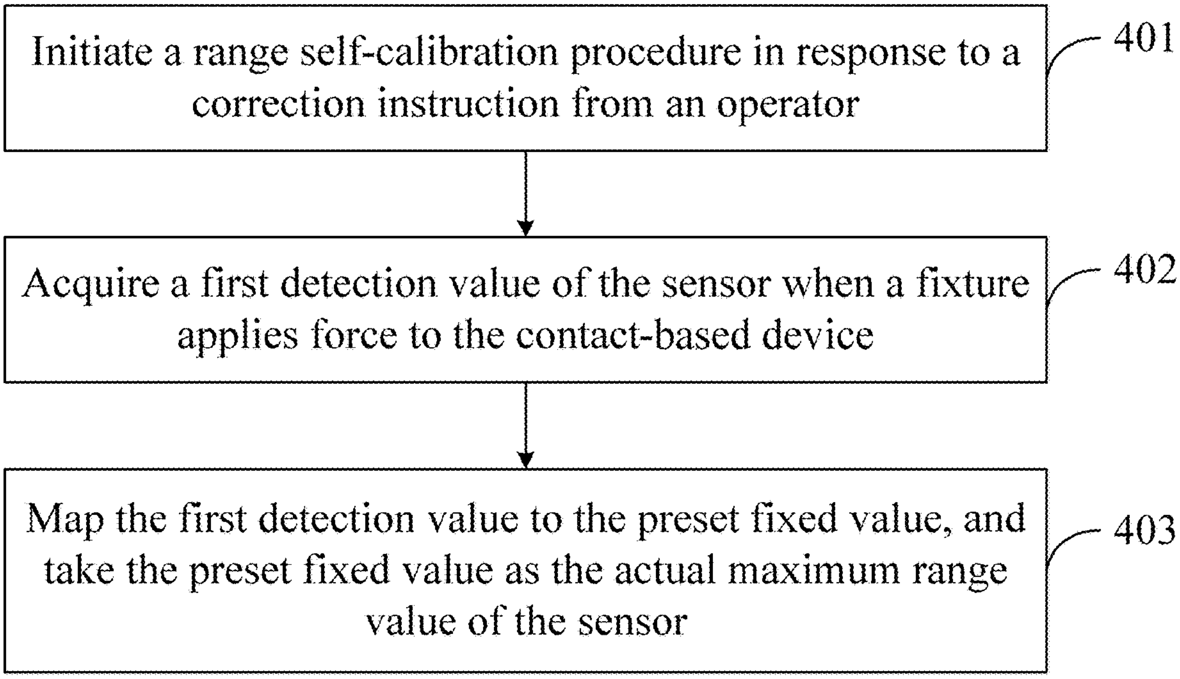
FIG. 4 is a flowchart of steps for a fourth sensor control method according to an embodiment of the present disclosure.

Optionally, with reference to FIG. 4, the method further includes Steps 401-403.

Step 401: initiating a range self-calibration procedure in response to a correction instruction from an operator.

Step 402: acquiring a first detection value of the sensor when a fixture applies force to the contact-based device.

Under standard conditions, the force applied by the fixture corresponds to a preset fixed value.

Step 403: mapping the first detection value to the preset fixed value, and taking the preset fixed value as the actual maximum range value of the sensor.

It should be noted that Steps 401-403 are essentially the same as those of Steps 301-303, except that Step 301 is triggered by the user, i.e., the range self-calibration is performed by the user during initial use or routine usage. In contrast, Step 401 is executed by the operator when the device leaves the factory. That is, the range self-calibration process in the present disclosure can be applied at different stages of the product, including before and after leaving the factory.

Figure 5:
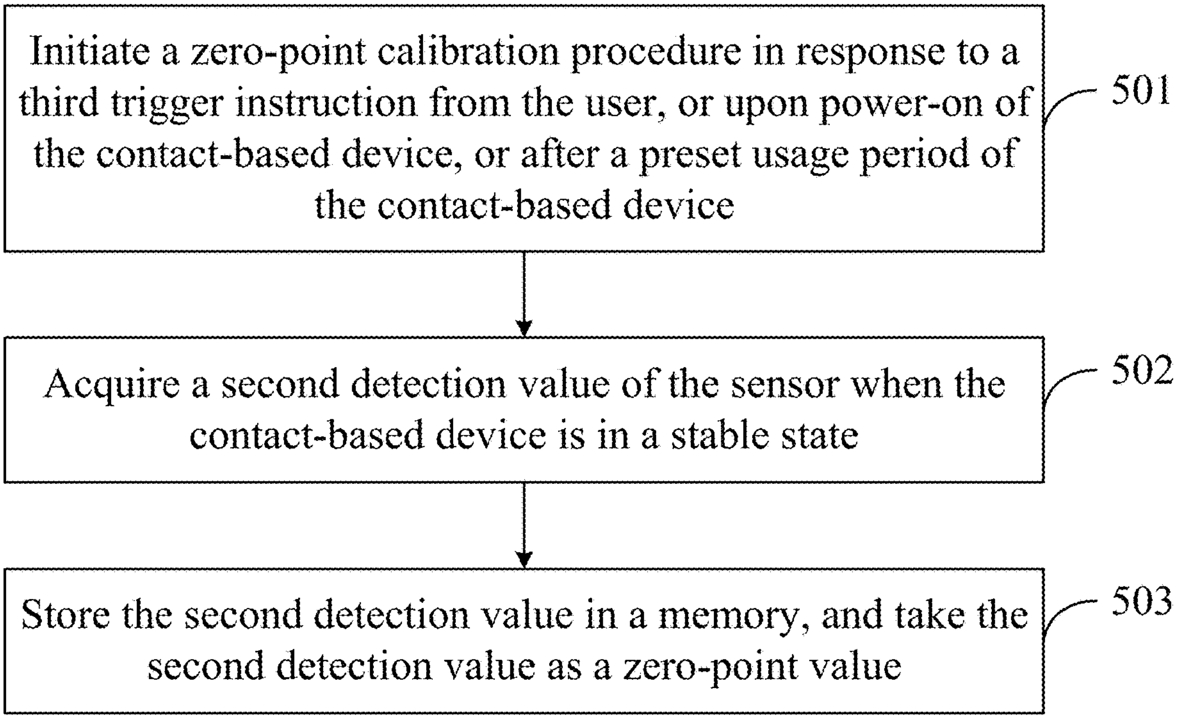
FIG. 5 is a flowchart of steps for a fifth sensor control method according to an embodiment of the present disclosure.

Optionally, with reference to FIG. 5, the method further includes Steps 501-503.

Step 501: initiating a zero-point calibration procedure in response to a third trigger instruction from the user, or upon power-on of the contact-based device, or after a preset usage period of the device.

It should be noted that when using a contact-based device, the user may actively trigger the contact-based device to initiate the zero-point calibration procedure. The zero-point calibration procedure is primarily used to perform the zero-point correction.

Specifically, a button may be provided on the contact-based device; and the third trigger instruction may be represented after the user press the button for a plurality of consecutive times. The times for pressing the button may be set according to actual demands, such as 2, 3, and 5.

It should be noted that the third trigger instruction is different from the first trigger instruction. For example, pressing the button twice in succession may correspond to the first trigger instruction, while pressing the button four times in succession may correspond to the third trigger instruction.

Of course, the zero-point calibration procedure may also be automatically triggered upon power-on of the contact-based device, or automatically triggered based on a preset time period at regular intervals. For example, the preset time period may be one month, three months, etc.

Step 502: acquiring a second detection value of the sensor when the contact-based device is in a stable state.

After then, acquiring a reading (that is, the second detection value) from the sensor when the contact-based device is in a stable state. The stable state may refer to a condition where the device is powered on but remains stationary, for example, after the device is turned on but before it is used by the user.

Step 503: storing the second detection value in a memory, and taking the second detection value as a zero-point value.

Considering that the sensor may have zero-point drift due to temperature, mechanical stress, or product aging, etc., the sensor is expected to output 0 N when there is no contact; however, a detection value of 3 N is acquired from the sensor. Therefore, the zero-point calibration procedure is performed to acquire the second detection value of the sensor when the contact-based device is in a stable state, and the second detection value is used as a new zero-point value. Through the method, a detection error caused by zero-point deviation can be corrected, thereby effectively maintaining the accuracy of the sensor.

Optionally, the method further includes: executing an initialization procedure to update the current maximum range value of the sensor in response to a fourth trigger instruction from the user.

It should be noted that when using a contact-based device, the user may actively trigger the contact-based device to update the current maximum range value of the sensor.

Specifically, a button may be provided on the contact-based device; and the fourth trigger instruction may be represented after the user press the button for a plurality of consecutive times. The times for pressing the button may be set according to actual demands, such as 2, 3, and 5.

It should be noted that the second trigger instruction is different from the fourth trigger instruction. For example, pressing the button twice in succession may correspond to the first trigger instruction, while pressing the button five times in succession may correspond to the fourth trigger instruction.

Figure 6:
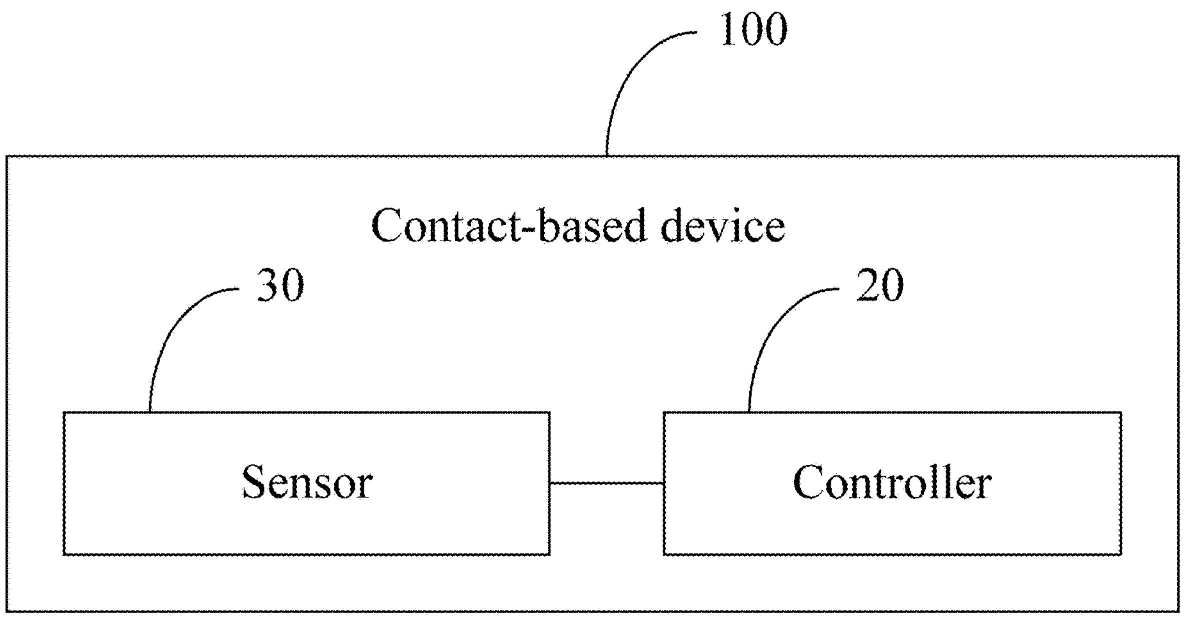
FIG. 6 is a block diagram of a contact-based device according to an embodiment of the present disclosure.
Figure 7:
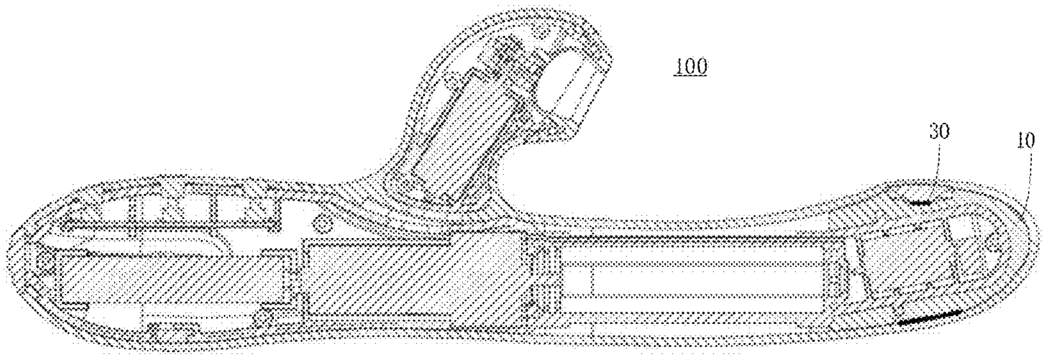
FIG. 7 is schematic structural diagram of a contact-based device according to an embodiment of the present disclosure.

With reference to FIGS. 6 and 7, based on the same inventive concept, this embodiment provides a contact-based device 100, including a main body 10, a controller 20, and a sensor 30.

Specifically, the controller 20 is disposed inside the main body 10, and the sensor 30 is disposed on the main body 10. The controller 20 is connected to the sensor 30, and the controller 20 is configured to perform the above sensor control method.

In this embodiment, the contact-based device 100 may specifically be a massager, which can be applied to different parts of the human body for massage, such as physiological parts, head, neck, and waist.

The sensor 30 may be, but is not limited to, a pressure sensor, a vibration sensor, or an inertial measurement unit, among others.

The controller 20 may be a central processing unit (CPU), or the controller 20 may be other general-purpose processor, digital signal processor (DSP), application-specific integrated circuit (ASIC), field-programmable gate array (FPGA), or other programmable logic device, discrete gate or transistor logic device, discrete hardware component, and the like. The general-purpose processor can be a microprocessor, or any conventional processor.

In addition, in the description of the specification and the appended claims of the present disclosure, the terms "first", "second", "third", etc. are merely for distinguish between descriptions and may not be understood as indication or implication of relative importance.

Reference in the description of the present disclosure to "an example" or "some examples", etc. means that one or more examples of the present disclosure include particular features, structures or characteristics described in combination with the examples. Accordingly, phrases such as "in one embodiment," "in some embodiments," "in other embodiments," and "in further embodiments," appearing in difference parts in the specification do not necessarily refer to the same embodiment, but rather mean "one or more but not all of the embodiments," unless specifically emphasized otherwise. The terms "include", "comprise", "have", and their variations mean "including but not limited to" or "comprising but not limited to", unless specifically emphasized otherwise.

In the description of the embodiments of the present disclosure, it should be understood that that "-" and "~" represent the same range of two numerical values, and the range includes end values thereof, for example, "A-B" means a range greater than or equaling to A and less than or equaling to B. "A~B" means a range greater than or equaling to A and less than or equaling to B.

In the description of the embodiments of the present disclosure, the term "and/or" represents merely an association relationship describing associated objects, indicating that there may be three types of relationships, for example, A and/or B, which means three types of situation, that is, the existence of A alone, the existence of both A and B, and the existence of B alone. In addition, the character "/" herein generally indicates that the associated objects are in an "or" relationship.

Although the embodiments of the present disclosure have been illustrated and described, it should be understood that those of ordinary skill in the art may make various changes, modifications, replacements and variations to the above embodiments without departing from the principle and spirit of the present disclosure, and the scope of the present disclosure is limited by the appended claims and their legal equivalents.

What is claimed is:

1. A sensor control method, comprising:

initiating an adaptive range determination procedure in response to a first trigger instruction from a user;

obtaining detection data of the sensor when the user is using a contact-based device; wherein the sensor is integrated into the contact-based device;

obtaining a maximum value of the detection data within a preset time period;

determining the maximum value of the detection data as a current maximum range value of the sensor; wherein the current maximum range value of the sensor is not greater than an actual maximum range value of the sensor;

controlling the contact-based device based on the current maximum range value of the sensor;

acquiring a maximum value of the detection data from each operation cycle in M operation cycles, wherein M is a positive integer; and dynamically updating the current maximum range value of the sensor based on the maximum value of the detection data from each operation cycle in M operation cycles.

2. The sensor control method according to claim 1, wherein the preset time period comprises N usage cycles, wherein N is a positive integer;

the obtaining a maximum value of the detection data within a preset time period comprises:

acquiring a maximum value of data from each of the N usage cycles; and calculating an average of N maximum values to obtain the maximum value of the detection data.

3. The sensor control method according to claim 2, wherein a weighted average strategy is used to calculate the average of N maximum values.

4. The sensor control method according to claim 3, wherein a closer a usage cycle is to a current time, a higher a weight is assigned.

5. The sensor control method according to claim 1, wherein the determining the maximum value of the detection data as a current maximum range value of the sensor comprises:

increasing the maximum value of the detection data by a preset ratio, and determining the value after increase as the current maximum range value of the sensor.

6. The sensor control method according to claim 5, wherein the value after increase is less than the actual maximum range value of the sensor, or when the value after increase is greater than the actual maximum range value of the sensor, the actual maximum range value of the sensor is determined as the value after increase.

7. The sensor control method according to claim 5, wherein a range of the preset ratio is 1%-20%.

8. The sensor control method according to claim 1, wherein the determining the maximum value of the detection data as a current maximum range value of the sensor comprises:

decreasing the maximum value of the detection data by the preset ratio, and determining the value after decrease as the current maximum range value of the sensor.

9. The sensor control method according to claim 8, wherein a range of the preset ratio is 1%-20%.

10. The sensor control method according to claim 1, wherein each operation cycle takes power-on and power-off of the contact-based device as cycle nodes.

11. The sensor control method according to claim 1, wherein the dynamically updating the current maximum range value of the sensor based on the maximum value of the detection data from each operation cycle in M operation cycles comprises:

increasing the current maximum range value of the sensor by a first preset value in response to a steadily increasing trend in the maximum value of the detection data of the sensor across each operation cycle in M operation cycles.

12. The sensor control method according to claim 1, wherein the dynamically updating the current maximum range value of the sensor based on the maximum value of the detection data from each operation cycle in M operation cycles comprises:

decreasing the current maximum range value of the sensor by a second preset value in response to a steadily decreasing trend in the maximum value of the detection data of the sensor across each operation cycle in M operation cycles.

13. The sensor control method according to claim 1, further comprising:

initiating a range self-calibration procedure in response to a second trigger instruction from the user or a correction instruction from an operator;

acquiring a first detection value of the sensor when a fixture applies force to the contact-based device; wherein under standard conditions, the force applied by the fixture corresponds to a preset fixed value; and mapping the first detection value to the preset fixed value, and taking the preset fixed value as the actual maximum range value of the sensor.

14. The sensor control method according to claim 1, further comprising:

initiating a zero-point calibration procedure in response to a third trigger instruction from the user;

acquiring a second detection value of the sensor when the contact-based device is in a stable state; and storing the second detection value in a memory, and taking the second detection value as a zero-point value.

15. The sensor control method according to claim 1, further comprising:

initiating a zero-point calibration procedure upon power-on of the contact-based device;

acquiring a second detection value of the sensor when the contact-based device is in a stable state; and storing the second detection value in a memory, and taking the second detection value as a zero-point value.

16. The sensor control method according to claim 1, further comprising:

initiating a zero-point calibration procedure after a preset usage period of the device;

acquiring a second detection value of the sensor when the contact-based device is in a stable state; and storing the second detection value in a memory, and taking the second detection value as a zero-point value.

17. The sensor control method according to claim 1, further comprising:

executing an initialization procedure to update the current maximum range value of the sensor in response to a fourth trigger instruction from the user.

18. A contact-based device, comprising: a main body, a controller disposed inside the main body, and a sensor disposed on the main body; wherein the controller is connected to the sensor; and the controller is configured to perform the following steps, comprising: initiating an adaptive range determination procedure in response to a first trigger instruction from a user; obtaining detection data of the sensor when the user is using a contact-based device; wherein the sensor is integrated into the contact-based device; obtaining a maximum value of the detection data within a preset time period; determining the maximum value of the detection data as a current maximum range value of the sensor; wherein the current maximum range value of the sensor is not greater than an actual maximum range value of the sensor; and controlling the contact-based device based on the current maximum range value of the sensor.

19. The contact-based device according to claim 18, wherein the sensor is a pressure sensor.

* * * * *